United States Patent [19]
Bolder et al.

[11] Patent Number: 6,077,524
[45] Date of Patent: *Jun. 20, 2000

[54] GASTRIC ACID BINDING CHEWING PASTILLES

[75] Inventors: Hermann-Josef Bolder; Faruk Imer, both of Köln, Germany

[73] Assignee: Bolder Arzneimittel GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,280

[22] PCT Filed: Apr. 20, 1995

[86] PCT No.: PCT/EP95/01493

§ 371 Date: May 16, 1997

§ 102(e) Date: May 16, 1997

[87] PCT Pub. No.: WO95/30407

PCT Pub. Date: Nov. 16, 1995

[30] Foreign Application Priority Data

May 6, 1994 [DE] Germany .............. 44 15 999

[51] Int. Cl.$^7$ .............. A61K 47/42; A61K 9/68
[52] U.S. Cl. .............. 424/441; 424/440
[58] Field of Search .............. 424/434, 440, 424/441; 426/573, 3, 74

[56] References Cited

U.S. PATENT DOCUMENTS

| | | | |
|---|---|---|---|
| 3,347,682 | 10/1967 | Rosenstein | 426/573 |
| 4,010,283 | 3/1977 | Canonne | 426/573 |
| 4,163,777 | 8/1979 | Mitra | 424/156 |
| 4,971,787 | 11/1990 | Cherukuri et al. | 414/48 |
| 5,591,473 | 1/1997 | McArdle | 426/573 |

*Primary Examiner*—Peter F. Kulkosky
*Attorney, Agent, or Firm*—Banner & Witcoff, Ltd.

[57] ABSTRACT

The subject matter of the invention is chewing pastilles based on at least partially or complete water soluble natural and/or synthetic polymers, selected from gums, alginates, carrageen, starch, pectin, and gelatin, which will form gels or viscous solutions in aqueous system, and additional adjuvants and additives, said pastilles containing antacids as active ingredients.

8 Claims, No Drawings

GASTRIC ACID BINDING CHEWING PASTILLES

The invention relates to chewing pastilles based on certain natural and/or synthetic polymers comprising antacids as active ingredients.

By the term pastilles there is generally understood—see also W. Rahn, Pharmazeutische Zeitung, pp 2214–2218 (1982)—preparations which can be sucked or chewed in the mouth. Namely, it is differentiated essentially between tablets, hard candies and gum pastilles (also designated as gum candies).

The processes for producing such dosage forms are basically distinguished from each other.

Tablets are pressed on tablet machines. To this end, the tablet mass has to be prepared by mixing and granulating. Several authors already have dealt with granulating methods for active substances which are difficult to process.

Candies are prepared by mixing saccharose and glucose syrup, boiling the resulting mixture at about 130° C., and removing most of the water from the mass in vacuo to a residual water content of from 0.5 to 2%. To the highly viscous candy mass cooled down to about 85° C. are added the active substances and flavors and admixed by kneading. With continuous cooling, the candy mass is drawn into strands, shaped, and cut in tapered rollers and other candy machines. It is known that, due to the viscosity of the candy mass, the distribution of the active substance is rather non-uniform.

Gum pastilles are prepared by initially dissolving in an agitator vessel hydrocolloids, e.g., gum arabic, together with saccharose, glucose syrup, sorbitol, xylitol, and the like in water, and dissolving, emulsifying or suspending the active ingredients in this base mass. The casting composition thus obtained is cast into so-called powder trays. These are, for example, flat wooden boxes of about 80×40 cm filled with starch, especially corn starch. The desired shapes are pressed into the smoothed powder using a stamp board, and the warm casting solution is exactly metered and pumped into the thus obtained wells, wherein the cast mass is not bound to the powder. Tray by tray, 500 to 1000 pastilles each, is thus cast, stacked, and water is removed from the pastilles in drying chambers to about 10% of residual moisture within 3 to 4 days. The pastilles thus produced are "depowdered" and then subjected to a final treatment.

The subject matter of DE 41 40 116 A1 is pastilles based on natural and/or synthetic polymers or fat-like substances with sugar and/or sugar substitutes, comprising poly (dimethyl siloxane) (Dimeticon, Simeticone), and a process for the preparation thereof.

According to Römpp Chemie Lexikon, 9th edition, page 200, 1989, the term "antacids" is used to mean substances which are to counteract hyperacidity of the gastric juice. Suitable compounds include magnesium hydroxide, magnesium oxide, magnesium carbonate, magnesium silicate, aluminum hydroxides, aluminum phosphate, magnesium aluminum silicates, hydrotalcite and magaldrate. Although, according to Römpp, the use of the prior sodium hydrogen carbonate and calcium carbonate should be desisted from, numerous commercial products are available which contain these components at least in minor proportions.

The object of the present invention as compared to the prior art has been to provide a novel single dosable dosage form of antacids using a casting process per se known from confectionery manufacture, which dosage form is characterized by: finest distribution of the active ingredient within the pastille, very accurate single dosing of the active ingredient, very easy handling of the active ingredient, especially convenient intake of the medicament, and optimum sustaining of the active ingredient in the stomach by the pastilles being slowly chewed.

The aforementioned object is achieved by pastilles based on at least partially or completely water soluble natural and/or synthetic polymers, selected from gums, alginates, carrageens, starch, pectin, and gelatin which form gels or viscous solutions in aqueous systems, and further adjuvants and additives, the pastilles containing antacids as active ingredients.

It has been found that the antacids, being in part water soluble and in part water insoluble, may be incorporated in an extraordinarily simple way in a finely dispersed form in pastilles based on the natural and/or synthetic polymers mentioned.

The term "pastilles" and particularly the term "gum pastilles" within the meaning of the present invention comprise those which are prepared by casting. Accordingly, the pastilles of the present invention consist of differently shaped elastic molded parts containing antacids in a finest distribution within a mixture of hydrocolloids and other adjuvants and additives. Gum pastilles are designated as solid solutions which upon sucking are retransformed to liquid solutions or dispersions. By means of the present invention, it is possible to achieve an exact single dosage of the pastilles with a relatively mild processing of the ingredients. With the mentioned, at least partially or completely water soluble natural and/or synthetic polymers, it is possible to achieve a particularly good incorporation of antacids as it is possible to work at relatively low temperatures. Thus, a particularly homogeneous distribution of the active substance in the total composition is created allowing the dosage of the active ingredient with standard deviations in the range of from 0.5 to 2%. In addition, it is possible according to the process of the present invention to produce antacids pastilles having a relatively high concentration.

Especially preferred natural and/or synthetic polymers within the meaning of the present invention are also known by the term of "hydrocolloids". Especially preferred are the gums selected from gum arabic, gelatin and tragacanth. In the same way, adjuvants and additives are preferably selected from sugar and/or sugar substitutes, hydrogenated fats, stearic acid, paraffins, oligosaccharides, polysaccharides and/or dextran.

Corresponding pastilles with other active substances are per se known in the prior art by the term of "gum pastilles". This name is derived from the raw material, gum arabic, incorporated therein. Also within the meaning of the present invention, this hydrocolloid is preferably used as a base material since it imparts good sucking and chewing properties to the pastilles.

Besides the polymers, the base mass in particular contains flavor-carrying substancves, such as sugar and/or sugar substitutes, since the patient is supposed to chew the pastille. Accordingly, it is necessary that the pastilles have such a good taste that they are not refused or swallowed down. To improve the taste, as known as such in the prior art, corresponding adjuvants are used, such as saccharose or its substitutes, such as fructose, hydrogenated glucose syrup, sorbitol, mannitol and/or xylitol, as well as known artificial sweeteners. In addition, taste corrigents and essences as well as ethereal oils may be used.

The relative amounts of the respectively necessary ingredients of the pastilles are less critical. Accordingly, the base mass contains, for example, from 2 to 80% by weight of the polymers, based on the total mass of the pastilles. Especially preferred is an amount of from 10 to 60% by weight or gum arabic or from 10 to 60% by weight of gelatin, respectively based on the total mass of the pastilles.

In a further preferred embodiment of the present invention, the pastilles contain from 20 to 50% by weight of sugar and/or sugar substitutes, based on the total mass of the pastilles. The amount of antacids may be varied within a wide range in the inventive pastilles. Preferably, the amount of antacids, based on the total formulation, should be as large as possible, at least to have an acid binding capacity of from 20 to 25 mval per unit dose.

Commercially available preparations, such as suspensions or chewing tablets, containing acid-binding active ingredients contain antacids having an acid binding capacity of from 10 to 25 mval. Accordingly, a particularly preferred embodiment of the present invention provides pastilles having an acid binding capacity of from 10 to 40 mval.

In the preparation of the pastilles, the above defined polymers, in particular, are contacted with water and other adjuvants and additives to form a gel or a viscous solution. Subsequently, antacids are suspended or dissolved in the base composition thus obtained, and this liquid composition is then cast into molds, dried either at room temperature or at an elevated temperature, especially from 40 to 70° C., preferably from 40 to 50° C., removed from the mold and subjected to final treatment.

For example, at the beginning of the preparation process, gelatin and gum arabic are dissolved in water and suspended together with antacids. This drug mixture is cast into so-called powder trays and dried, separated from the powder and subjected to final treatment as previously described. The particular advantages of the inventive pastilles and of the process for the preparation thereof are a low temperature load of the adjuvants and active ingredients, the complete homogeneity thereof in the casting mass which enables the active ingredient to be dosed with high accuracy, and most important of all, the excellent chewability as compared to tablets, and the improved taste, each of which are advantages promoting the compliance of the patient.

We claim:

1. Gum pastilles prepared by dissolving in water at least partially or completely water soluble natural and/or synthetic polymers selected from the group consisting of gums, alginates, carrageen, starch, and pectin, which polymers are hydrocolloids and form gels or viscous solutions in aqueous systems, and additional adjuvants and additives, and dissolving, emulsifying, or suspending antacids into the resulting solution such that said antacids are homogeneously distributed in the pastille, said antacids having an acid binding capacity of from 10 to 40 mval per unit dose wherein the pastilles comprise from 2 to 80% by weight of the polymers based on the total mass of the pastilles.

2. The pastilles according to claim 1 wherein the chewing pastilles are based on at least gums selected from gum arabic or tragacanth.

3. The pastilles according to claim 1 wherein the adjuvants and additives are selected from the group consisting of sugar, sugar substitutes, hydrogenated fats, stearic acid, paraffins, oligosaccharides, polysaccharides, dextran, and mixtures thereof.

4. The pastilles according to claim 3 comprising sugar substitutes selected from the group consisting of fructose, sorbitol, mannitol, xylitol, hydrogenated glucose syrup, artificial sweeteners, and mixtures thereof.

5. The pastilles according to claim 2 wherein the pastilles comprise from 10 to 60% by weight of gum arabic based on the total mass of the pastilles.

6. The pastilles according to claim 4 wherein the pastilles comprise from 20 to 50% by weight of sugar substitutes based on the total mass of the pastilles.

7. The pastilles according to claim 1 wherein the antacids have an acid binding capacity from 10 to 25 mval per unit dose.

8. The pastilles according to claim 1 wherein the antacids are selected from the group consisting of aluminum hydroxides, aluminum phosphates, magnesium hydroxide, magnesium oxide, magnesium carbonate, magnesium silicate, magnesium aluminum silicates, hydrotalcite and magaldrate, sodium carbonate, calcium carbonate, and mixtures thereof.

* * * * *

UNITED STATES PATENT AND TRADEMARK OFFICE
CERTIFICATE OF CORRECTION

PATENT NO. : 6,077,524
DATED : June 20, 2000
INVENTOR(S) : Hermann-Josef Bolder, et al.

It is certified that error appears in the above-identified patent and that said Letters Patent is hereby corrected as shown below:

On the title page, item [54] and column 1:

In the Title:
"Gastric Acid Binding Chewing Pastilles" has been replaced with
--Chewable Anti-Gastric Acidity Pastilles--.

In the Abstract, line 2:
"complete" has been replaced with --completely--.

Signed and Sealed this

Eighth Day of May, 2001

*Attest:*

NICHOLAS P. GODICI

*Attesting Officer*   Acting Director of the United States Patent and Trademark Office